United States Patent
Reavell et al.

(10) Patent No.: US 6,828,794 B2
(45) Date of Patent: Dec. 7, 2004

(54) ELECTROSTATIC PARTICLE MEASUREMENT

(75) Inventors: Kingsley St John Reavell, Clare College (GB); Nicholas Collings, Cambridge (GB)

(73) Assignee: Cambustion Limited, Cambridge (GB)

( * ) Notice: Subject to any disclaimer, the term of this patent is extended or adjusted under 35 U.S.C. 154(b) by 0 days.

(21) Appl. No.: 10/280,176

(22) Filed: Oct. 24, 2002

(65) Prior Publication Data

US 2004/0080321 A1 Apr. 29, 2004

(51) Int. Cl.[7] .............................................. G01N 27/66
(52) U.S. Cl. ...................... 324/464; 324/71.1; 324/458
(58) Field of Search ................. 324/464, 71.1, 324/71.4, 458, 452–453; 422/82.03, 82.04

(56) References Cited

U.S. PATENT DOCUMENTS

| 4,652,866 | A | * | 3/1987 | Siegmann et al. | .......... 340/628 |
| 5,281,915 | A | * | 1/1994 | Takahama et al. | .......... 324/464 |
| 5,576,617 | A | * | 11/1996 | Webb et al. | ................ 324/71.4 |
| 5,644,220 | A | * | 7/1997 | Urs et al. | ................... 324/71.3 |
| 6,433,553 | B1 | * | 8/2002 | Goeckner et al. | .......... 324/464 |

* cited by examiner

Primary Examiner—Anjan K. Deb
(74) Attorney, Agent, or Firm—Barnes & Thornburg LLP

(57) ABSTRACT

An electrostatic instrument for measuring particle concentrations and possibly sizes in aerosols, such as an Electrostatic Low Pressure Impactor or Differential Mobility Analyser suffers from errors which limit the useful response bandwidth of the device. The invention minimises or eliminates these transient errors which are caused by changing particle concentrations in the aerosol. A system may be added to an otherwise conventional instrument to compensate for the transient effects based on a model of the charge production mechanism. Alternatively, a screening electrode placed over the sense electrodes in the instrument, and held at controlled electrical potential difference, is added to the instrument to eliminate the effect. A third embodiment adds compensating electrodes which provide a direct measurement of the transient effect which can be subtracted from the signal.

22 Claims, 6 Drawing Sheets

ELECTROSTATIC PARTICLE MEASUREMENT

FILED OF THE INVENTION

This invention relates to apparatus for and method of analysing a mixture comprising a fluid and a plurality of electrically charged particles contained therein.

BACKGROUND OF THE INVENTION

Particle concentrations in aerosols (a suspension of particles in a gas) are often measured by electrostatic techniques based on the principle of charging the particles in a sample of the aerosol and collecting them on one or several collection elements such as electrodes or filters. The current flowing to these electrodes or filters, here referred to as "collection electrodes", is measured and indicates the quantity of particles collected and hence their concentration in the aerosol.

The particles may be charged by any one of a number of methods, such as ultraviolet irradiation or corona discharge; or natural charging (often associated with a combustion process) may be relied upon.

Frequently, differences in mobility (the readiness of particles to diff-use or drift through the gas) are used to separate different sizes of particles before collecting them on the collection electrodes. Some devices alternatively use differences in momentum for this discrimination.

Such devices are used to make measurements of the number of particles and sometimes the spectrum of particle sizes in aerosols, but are limited to resolving accurately only relatively slow changes in the particle concentration. This is because faster changes lead to transient discrepancies between the actual particle concentration and the measured current which are caused by the rate of change of the concentration of charged particles in the aerosol near the detectors.

SUMMARY OF THE INVENTION

According to the present invention, modifications are made to the design of electrostatic particle measurement instruments to compensate for or eliminate the transient currents produced by the rate of change of charge near the sensing electrodes, and hence reduce the transient errors in measured particle concentrations.

According to a first aspect of the invention, this is achieved by apparatus for analysing a mixture comprising a fluid and a plurality of electrically charged particles therein, the apparatus comprising a collection element for collecting said particles and providing an output relating to the number of particles incident thereon, and compensation electrode means, spaced from the collection element, which is responsive to charged particles which pass in the vicinity of, but which are not collected by, the collection element, thereby to enable the output from the collection element to be used to determine the charge collected by the collection element.

Thus, by providing compensation electrode means the invention enables spurious measurements caused by particles which induce a current in the collection element, but are not themselves collected by that element, to be avoided. The collection element may comprise any suitable element for collecting charged particles so that the total charge or current resulting from the collection of charged particles can be measured.

For example, the apparatus may comprise an electrostatic low pressure impactor (ELPI) instrument which charges the particles in an aerosol to be measured and then passes the aerosol through a column of impactors. The impactors comprise perforated plates followed by collection plates which may be covered with grease. When the aerosol passes through the perforations, relatively massive particles are forced by their momentum to hit the collection plates where they are detected whereas the lighter particles are carried by the gas flow to the subsequent stages. The size of the perforations, size of the plates and the operating pressure are varied throughout the column such that the largest particles are detected on the earliest collection plates and successively smaller particles are detected on later collection plates. Measurement of the electrical current flowing to these collection plates indicates the number of particles detected by each and hence the concentration of size class of particles. Each collection plate thus functions as an electrode.

Alternatively, the apparatus may have a collection element which comprises an electrode to which is applied an accelerating voltage for attracting the charged particles. The apparatus may have a succession of such electrodes arranged along a conduit so as to provide an output representative of the size spectrum (i.e. the concentration of particles in each of a number of size classes).

In such a case, the compensation electrode means may to advantage comprise a shielding electrode which overlies each of the collection electrodes, the arrangement being such that charged particles on the other side of the shielding electrode from the collection electrodes are prevented or inhibited by the shielding electrode from inducing currents on the collection electrodes.

The shielding electrode may to an advantage comprise a conductive grid. Preferably, the conduit is cylindrical, each collection electrode is annular and is coaxial with said cylinder and the shielding electrode is also cylindrical and coaxial with the conduit.

Instead of shielding the collection electrode, the compensation electrode means may alternatively be so arranged as to provide an output which can be processed to provide a correction signal for removing or inhibiting components of the output from the collection electrode caused by induced current.

Such a compensation electrode means can be controlled so as to be maintained at a voltage which results in a collection of no significant number of particles. Alternatively, the compensation electrode means may collect all of the particles which pass in the vicinity of the collection electrode without being collected by the latter.

In arrangements which have a plurality of collection electrodes distributed along a conduit, the compensation electrode means for a given collection electrode may be constituted by all of the collection electrodes positioned downstream thereof. If the downstream collection electrodes between them, collect all of the particles which are not collected by the first said collection electrode, their outputs can be used to obtain an indication of the induced current on said collection electrode.

According to a second aspect of the invention, in a method of measuring the current flow to a collection electrode to indicate the quantity of charged particles in an aerosol, there is an improvement comprising the step of eliminating or compensating for the part of the current flowing to said collection electrode which is caused by the rate of change of charged density in said aerosol near said collection electrode.

BRIEF DESCRIPTION OF THE DRAWINGS

Three embodiments of apparatus and methods in accordance with the invention will now be described by way of example only and with reference to the accompanying drawings in which.

DETAILED DESCRIPTION

First Embodiment

Figure 1:
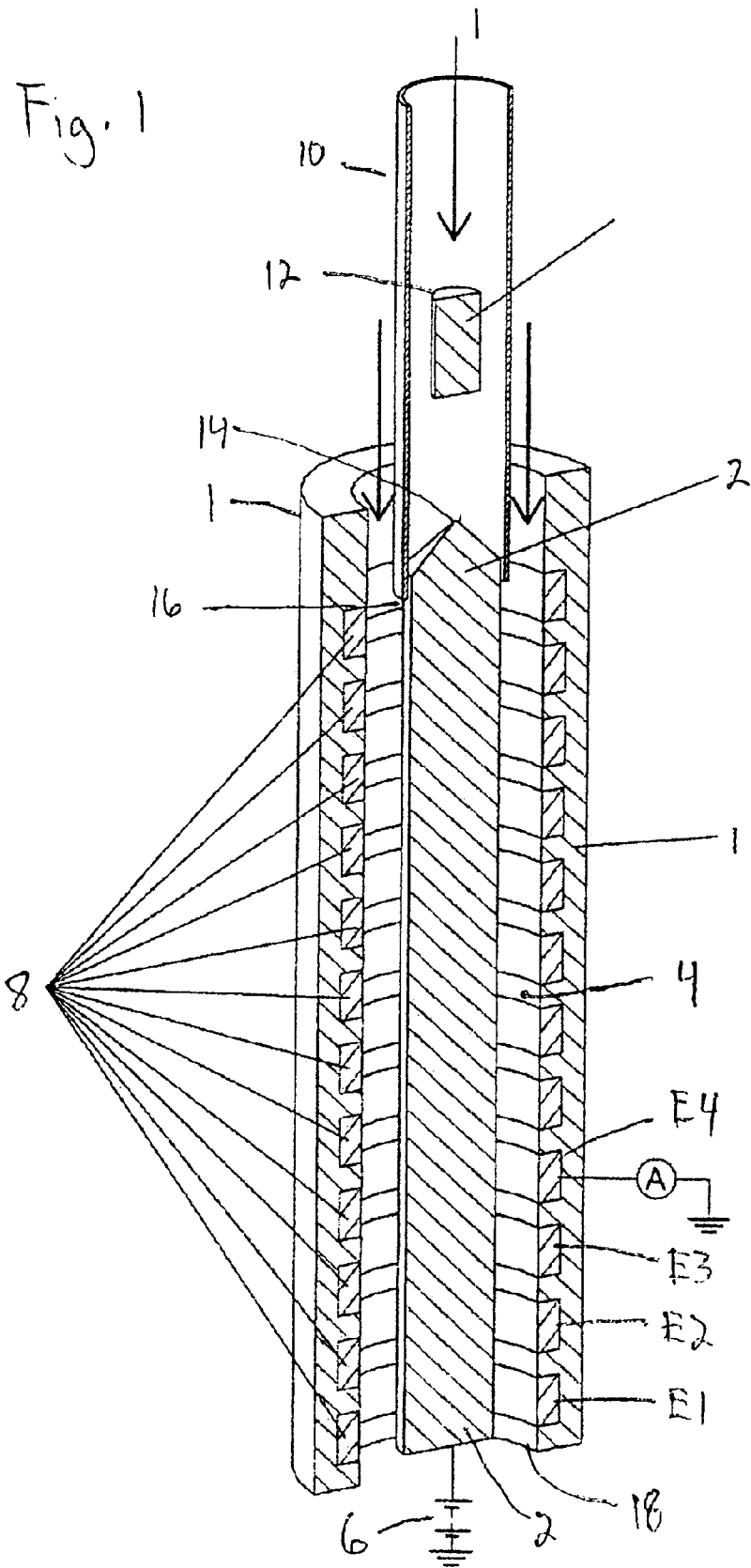
FIG. 1 is a cutaway diagram of a Differential Mobility Spectrometer (DMS) forming part of the first embodiment of apparatus in accordance with the invention.

The DMS shown in FIG. 1 is used to analyse aerosols, and comprises a hollow cylindrical outer casing 1 formed from an insulating material and which contains a solid cylindrical central electrode 2 which is coaxial with the housing 1. The electrode 2 is spaced from the inner walls of the housing so as to define with the housing an annular conduit 4 extending along the length of the housing 1. The electrode 2 is held at a positive potential by a voltage source 6 connected thereto. The inner wall of the housing 1 is provided with a series of annular, axially spaced recesses which are coaxial with the housing 1 and electrode 2, and each of which houses a respective annular collection electrode (collectively denoted by reference numeral 8).

An inlet pipe 10 extends into one end of the housing 1, and contains a particle charging device 12. The pipe 10 is coaxial with the electrode 2. As can be seen from FIG. 1, the pipe 10 fits over the end of the electrode 2, which end has a conical portion 14. However, the pipe 10 has an inner radius which is slightly larger than the radius of the electrode 2 so that the pipe 10 is spaced from the electrode 2 to define an annular inlet 16 for the aerosol to be analysed by the DMS. All of the collection electrodes 8 are, in use, held at earth potential, but for the sake of simplicity, the connection to earth is only shown in relation to one of those electrodes, labelled E4. Also specifically labelled are the electrodes E1, E2 and E3 which, together with E4, constitute the last four collection electrodes that a sample of aerosol passes on its way through the device from the inlet 16 through to the outlet 18 defined by the space between the bottom of the electrode 2 and the housing 1.

Figure 2:
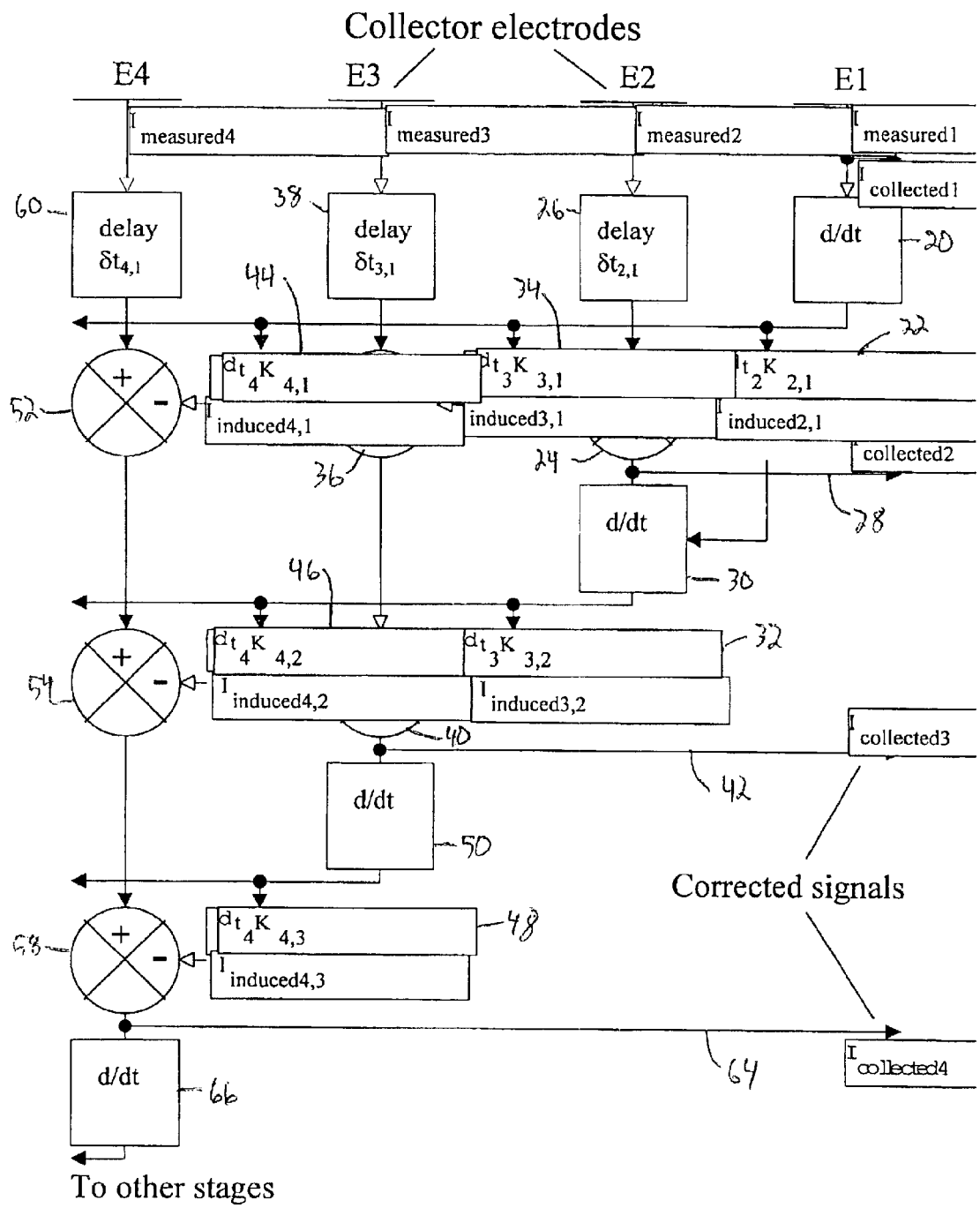
FIG. 2 is a functional block diagram illustrating processing means connected to the DMS of FIG. 1.
Figure 3:
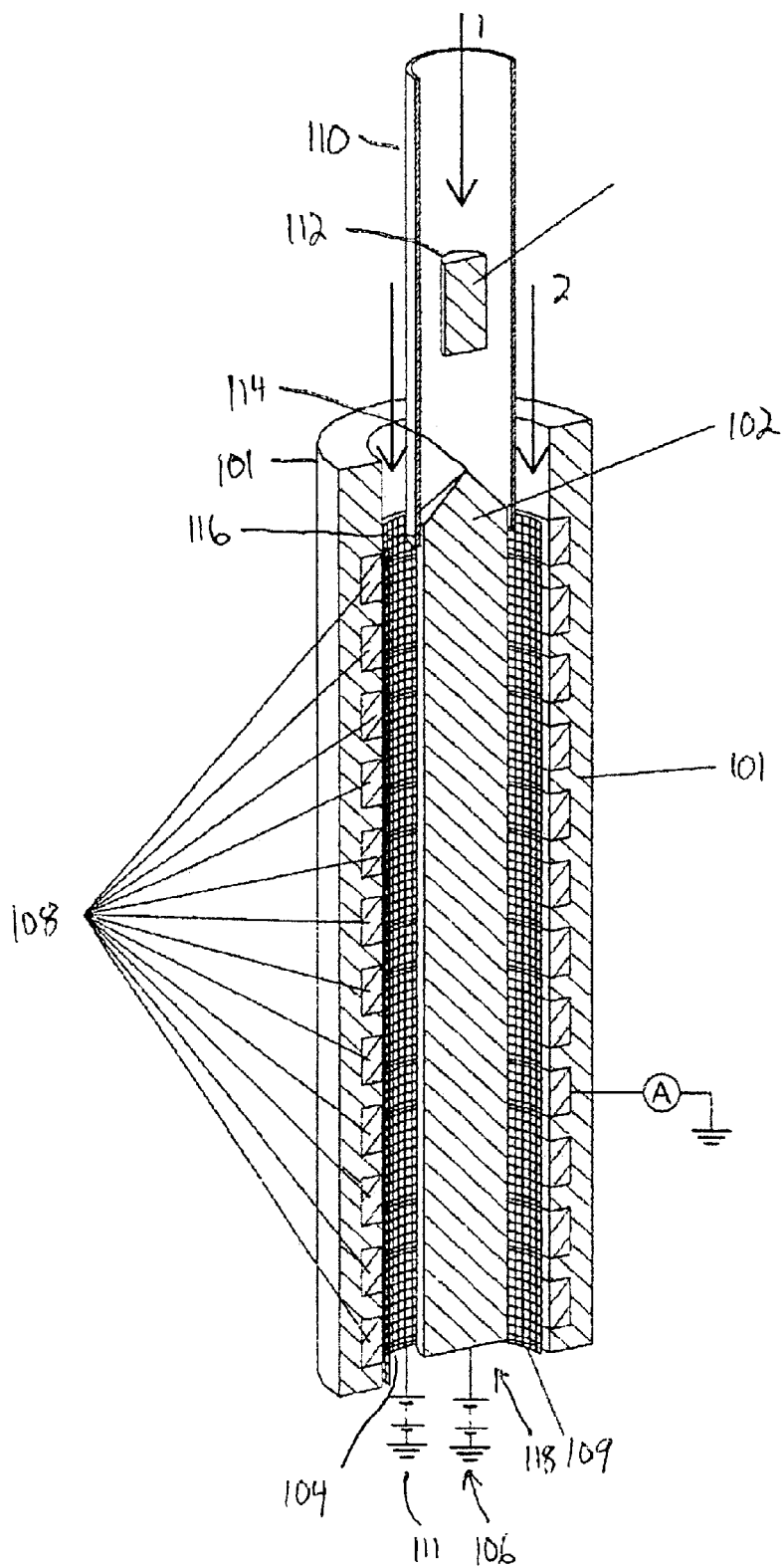
FIG. 3 is a cutaway diagram of the a DMS of the second embodiment of apparatus the DMS having a shielding electrode.

The collection electrodes 8 are connected to signal processing means, as shown in FIG. 2, which is specifically adapted to compensate for currents induced in the electrodes 8 as the result of the change in number density of particles passing through the conduit.

For the sake of conciseness, the signal processing means is only shown in relation to the electrodes E1–E4, but it will be apparent from this description how the signal processing means interacts with each of the other electrodes 8. The output of the electrode E1 is connected to calculating means comprising a differentiator 20 the output of which is connected to a calculation device 22 for determining from the output of the differentiator the current which would have been induced on the electrode E2 by the charges collected on E1.

The output of the calculation device 22 is fed to an adder 24 in which the value for the induced current is subtracted from the current measured on the electrode E2 at a given time before the output on the electrode E1 was measured so that the measured induced current and the measured output from the electrode E2 are synchronised when fed to the adder. This synchronisation is achieved with the aid of delay circuitry 26 which comprises a memory for storing a succession of measured current values from the electrode E2 and supplying them after a pre-determined delay to the adder 24. The output of the adder 24 provides a signal representative of the current collected on the electrode E2 (as indicated at 28), and this can be fed to a further differentiator 30 for determining the rate of change of charge collected on E2.

The output from the differentiator 30 is fed to further calculation device 32 which determines the current which was induced on the electrode E3 as the result of change of number density of those charged particles subsequently collected on E2. The output of the differentiator 20 is also connected to a further calculator 34 which determines the current which would have been induced on the electrode E3 by the charges collected by E1. This value is fed to an adder 36, the other input of which is connected to a further delay device 38 which is similar in form and function to the device 26. The output of the adder 36 is fed to a further adder 40, the other input of which is connected to the output of the calculation device 32 so that the output of adder 40 is representative of the current caused by charges collected by the electrode E3, which is output as indicated at 42.

Similarly, the calculation means comprises farther calculation devices 44, 46 and 48 and a further differentiator 50 which calculate the components of current induced on E4 attributable to the charges collected on E1–E3, and those components are subtracted (in adders 52, 54 and 58) from the output of the delay circuitry 60 connected to E4 so as to produce an indication of the current collected on E4 (as represented by reference numeral 64) the output of the adder 58 is connected to a further differentiator 66.

Considering now all of the collection electrodes in the DMS, the output from each of these electrodes (other than the first electrode, closest to the input) is connected to a respective differentiator, the output of which is in turn, connected to a respective series of calculation devices, each of which calculates the induced current, attributable to the charge collected on the collection electrode connected to that differentiator, on a respective one of the upstream electrodes. The output of each of the electrodes is also connected to a suitable delay device for synchronising the output of that electrode with the induced current values which are fed to each of the adders (each corresponding to a respective downstream electrode) connected to that delay device.

Thus, for each electrode other than E1, the charge collected on the or each downstream collection electrode is used to provide a correction to take into account the current which is induced by charges passing in the vicinity of the electrode (but which are not collected thereby).

This embodiment of this invention uses a system added to or incorporated in a particle measuring instrument and corrects for the effects of the rate of change of charged particle concentration, which is estimated from the variation over time of the currents measured on the collection electrode or electrodes. This embodiment may be used where a sample of the aerosol to be measured, which may optionally be diluted flows past or through the collection electrode or electrodes which are connected to a current measuring electrical circuit. This embodiment is preferably used in situations in which all or a fixed proportion of the total number of charged particles in the aerosol are collected on the collection electrodes.

The correction for the effects of the rate of change of charged particles concentration is based on the following model for the mechanism of current generation.

A charged particle near an electrode held at a fixed potential attracts a charge of the opposite sign onto the electrode from the connected circuit. The quantity of charge attracted is proportional to the charge on the particle but it is also a function of its distance from the electrode and the geometry of the other conductors nearby. As the particle approaches the electrode the charge attracted to the electrode increases and therefore there is a current flow in the connected circuit When the particle finally reaches the electrode, the total attracted charge due to that particle is equal and opposite to its charge. Therefore, when a large number of particles steadily flowing to the electrode is considered, the current measured is as if it were just produced at the time the particles were collected.

It will be appreciated that the particle is collected in the sense that it comes into contact with the electrode so that a charge can be exchanged between the particle and the electrode. The particle is not necessarily retained on the electrode.

If the concentration of charged particles in the aerosol near the electrode changes, however, this will lead to a change in the charge induced on the electrode and therefore an extra component of current in the connected circuit before the particles at the new concentration reach the electrode. If the change in concentration is a reduction, the magnitude of charge on the electrode will reduce producing a component of current in the opposite direction from that produced by collected particles.

Using this model, we can see that any current measured to the collection electrode is due to the sum of the effects of collected particles, new charged particles entering the vicinity of the electrode and those charged particles already near it approaching, less the effect of any particles which leave tile vicinity of the electrode. This embodiment of the invention uses this to estimate accurately the concentration of particles in the aerosol at any instant without errors which come from ignoring the effect of changing charge concentration near the electrode.

The sample aerosol flow 1 is passed through the charging device 12, which applies a positive charge to the particles, and then flows along the centre of an annular channel surrounded by a sheath flow of clean gas entering between the inlet pipe 10 and housing 1 at the same flow velocity. While this happens the electrode 2 is held at a high positive potential, and the current flow from the collection electrodes 8 is measured. The collection electrodes 8 and centre electrode 2 set up an electrical field in the annular conduit 4 which causes the positively charged particles to drift from the sample aerosol, through tie sheath flow, towards the electrodes 8. The smaller particles, with less aerodynamic resistance, drift faster, reaching the outside of the channel sooner and being collected on an electrode further upstream than the larger particles. For this embodiment of the invention to be applied to the DMS, either the voltages, flow rates and geometry of the instrument should be designed such that almost all the particles in the aerosol are collected before the flow exits the channel. In a modified version of this embodiment, additional mesh, gauze or functionally equivalent, electrodes are mounted at the exit end to collect any remaining particles, the current flow from these electrodes also being measured. (such an additional element would be treated as electrode E1).

Generally more particles pass through an upstream collection electrode ring than are collected on it, so changes in the concentration of these larger particles which pass through can dominate the current from the particles actually collected on an upstream collection electrode. The signal processing means shown in FIG. 2 act as a correction system. The collection electrodes E1 and E4 in this diagram are the four most downstream of the collection electrodes in FIG. 1. E1 is the collection electrode furthest downstream.

As very few charged particles leave the channel without being measured, the current on collection electrode E1 indicates the number of particles per unit time ('particle flux') in the aerosol that passed through the previous electrode E2 uncollected. To correct for the transient errors due to the change in particle concentration in the vicinity of E2, therefore, the rate of change of the current on E1 (shown by the d/dt box) is multiplied by a constant of proportionality and subtracted from the current measured on E2. Preferably, this correction is applied to the value of the current measured on the penultimate electrode E2 a short period earlier and stored, as indicated by the delay blocks in FIG. 2; this delay period being equal to the time taken for the aerosol and sheath flow to travel from the average position of the penultimate electrode to that of the final electrode.

Practically, the differentiation operation d/dt may be approximated, for example by finite difference The product $\delta t_2 K_{2,1}$ is the constant of proportionality between the rate of change of particle flux and the correction applied to the penultimate electrode. Both elements of the product are defined below. Preferably, the constant of proportionality is the integral over time of the influence factor along the path followed by the charged particle. The constant of proportionality may, alternatively, be derived from measurements of the particular instrument.

The influence coefficient of a charged particle near an electrode is the ratio of the magnitude of charge attracted onto the electrode by the charged particle divided by the charge on the particle. It is a function of the distance of the particle from the electrode and the geometry of the electrode and other conductive bodies (such as the centre electrode in the DMS) nearby. This can be calculated for the particular geometry of the instrument by conventional techniques such as Gauss's law and the principle of overall charge neutrality or widely available computer programmes.

The radial location of a charged particle at the penultimate ring can be estimated from the forces applied to it as it passes through along the channel 4. The most important forces are aerodynamic and the electrostatic forces due to the applied electric field and charge image attraction to surfaces. For the DMS, the applied electric field Is large and therefore dominates the charge image effects in the bulk of the column. The radial entry location is approximately known, as the aerosol all enters near the centre of the channel, and one other point on the path is known to be the location of the final electrode. The electric field can be calculated from Gauss's law.

Along with Stokes' theorem (strictly modified by a Cunningham slip correction factor for these small particles) which states that the drift velocity of a particle is proportional to the force on it, this allows the path the particle follows through the channel to be predicted and thus the influence coefficient of any collected particle on any upstream ring to be evaluated. In FIG. 2, the coefficient $\delta t_m \kappa_{m,n}$ the influence coefficient of particles collected at collection electrode Em on the charge on collection electrode En, multiplied by the time they spend in the vicinity of electrode En.

When this correction is applied to the current from the penultimate electrode E2, this then gives an accurate reflection of the particle flow collected at that electrode. Therefore, in the same way, the current measurement on the next electrode E3 can be corrected for the change in particle concentration of particles collected at both downstream rings E1 and E2 (separately, as the radial location and hence coefficient $\delta t_m \kappa_{m,n}$ of the two sizes of particles will be different at the axial position of the upstream electrode). The same process is then applied successively to all upstream electrodes each of which is corrected for the currents collected on all the downstream electrodes.

The operation of the DMS and the theory behind correction of detected currents will now be described in more detail. An aerosol formed of a spectrum of particle sizes from less than 5 nm to around 1000 nm at a flow rate of around 5 litres/min STP is charged in a prescribed manner and the resulting charged aerosol is classified according to electrical mobility in the annular column in the housing 1. The size and number of the particles in the aerosol is inferred from the currents measured at various locations within the D)MS. The currents measured on the collection electrodes (typically >1>10$^{-15}$ A) can have a significant component which is due to the rate of change of charged particles entering the classifier. Methods to obtain a measurement which improves the accuracy of the classification are presented.

The aerosol is drawn into the instrument using a vacuum pump (not shown) with a swept capacity of about 25 m$^3$/hr. Particles larger than about 1000 nm are collected on an impactor such that only particles less than 1000 nm are admitted to the instrument. The sample is then drawn through a restrictor such that the sample pressure is reduced from near to atmospheric pressure, to about 250 mbar.

Aerosol particles are charged in a unipolar diffusion charger with a residence time of around 500 ms and an average ion density of 1×10$^{13}$/m$^3$. The sample flow of charged particles is admitted to the entry of the classifier in a cylinder immediately adjacent to the high Voltage electrode and is surrounded by a cylinder of the clean sheath air. The ratio of the sample flow to sheath flow is about 4:1. A section of the classifier is shown schematically in FIG. 5.

The particles move with the local gas flow speed at about 1 m/s, but experience a force due to a strong electric field maintained between the High Voltage electrode 2 and the collector electrode E2 which is held near to earth potential. The electric field strength is in the range 0–10 kV/cm (High Voltage electrode voltage range is 0–10 kV) and the Current flows to the Collector electrodes are measured with sensitive electrometer amplifiers which are generally operated at near ground potential.

Column lengths of about 1 m, comprising 22 or 26 Collector electrodes with lengths of 15–35 mm and internal diameter about 55 mm have been found to give good performance. The diameter of the High voltage electrode of about 25 mm gives an annular gap of 15 mm. The ratio of sheath air to sample flow of around 4:1 has been used.

Theory

Figure 5:
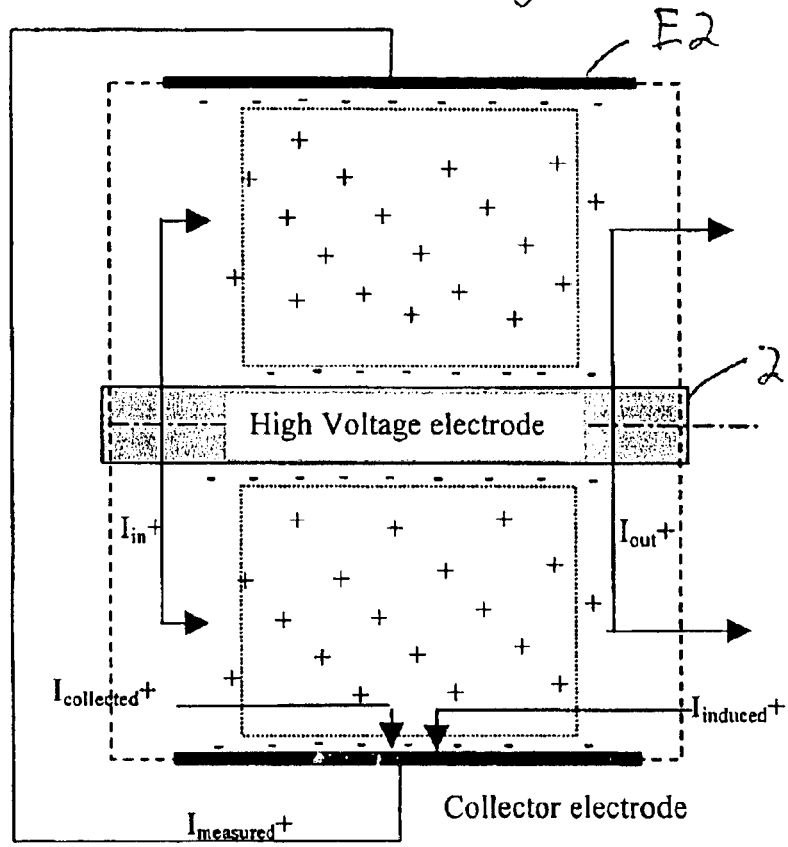
FIG. 5 is a schematic diagram of a part of the DMS of FIG. 1, and illustrates how charged particles can make different contributions to the current collected on a collection electrode of the DMS.

Consider the toroidal control volume bounded by the dotted box shown in FIG. 5 within the classifier and excluding the High Voltage electrode. The electric field force causes charged particles to drift outwards and some of the particles will hit the Collector electrode. In FIG. 5 the flow of charged particles into the control volume is $I_{in}$; the flow of particles out of the control volume is $I_{out}$; the flow of charge from particles incident on the Collector electrode leads to $I_{collected}$; the flow of induced charge to the Collector electrode leads to $I_{induced}$; the total charge flow to the Collector electrode is $I_{measured}$; the total of the positive charge within the volume is $\Sigma+$ and the total of the negative charge within the volume is $\Sigma-$.

Positive charge in the sample flow, $\Sigma+$ causes an equal and opposite negative charge to be induced, $\Sigma-$. This negative charge is split between the surface of the High Voltage electrode and the Collector electrode such that the potential difference between the High Voltage electrode and Collector electrode is unchanged.

$$\Sigma^- = \Sigma^-_{collector} + \Sigma^-_{HVelectrode} \qquad 1$$

We may describe this split by a constant K which is solely a function of the radial distribution of the positive charge such that. K is known as the influence coefficient:

$$K = \frac{\sum -\text{collector}}{(\sum -\text{collector} + \sum -HVelectrode)} = fn\left(\text{radial location of } \sum +\right) \qquad 2$$

Neglecting charge flow to the High Voltage electrode (which can only occur by diffusion against the strong electric field), the charge flow to the Collector Electrode carried by particles is given by:

$$I_{collected} = I_{in} - I_{out} \qquad 3$$

Consider a cylindrical surface bounded by the dashed line in FIG. 5 which is located within the conductive Collector electrodes. The axial field is constant. Gauss's law states:

$$\oint E \cdot ds = \int_{volume} q\, dv \qquad 4$$

Where:

q is the charge in the volume enclosed by the surface

E is the electric field normal to the surface and $\oint ds$ is the integral over the surface The surface comprises a cylinder and 2 circular ends. Therefore Gauss's Law may be expressed as:

$$\text{Area}_{circular\ ends} \times E_{axial} + \text{Area}_{cylinder} \times E_{radial} = \Sigma q \qquad 5$$

Since the cylindrical surface is located inside the conductive Collector electrode, there is no field normal to this surface. Therefore:

$$\text{Area}_{circular\ end} \times E_{axial} = \Sigma q = \Sigma^+ + \Sigma^- \qquad 6$$

Therefore, substituting from 1 and 2

$$\Sigma^-_{collector} = K \cdot (\text{Area}_{circular\ ends} \times E_{axial} - \Sigma^+) \qquad 7$$

Changes in $\Sigma^+$ at fixed r and hence fixed K cause the inducing of a current in the Collector electrode of the form:

$$I_{induced} = d\Sigma^-_{collector}/d_1 = -K^{d(\Sigma+)}/dt \qquad 8$$

Therefore the total charge flow to the collector electrode, $I_{measured}$ has two components $I_{collected}$ and $I_{induced}$. For the application described here, the required measurement of the classifier is $I_{collected}$, which corresponds to impact of charged particles within a small band of electrical mobility such that their trajectories are incident onto the collector electrode.

The charge flow $I_{induced}$ has a component from all particles within the control volume and is an unwanted artifact in this application. In certain circumstances, the magnitude of $I_{induced}$ can be significantly higher than $I_{collected}$. In particulars collector electrodes near the entry of the column may have a small incident charge and a high induced charge, since most of the charged particles pass the electrode without hitting it.

In general:

$$I_{measured} = I_{collected} + I_{induced}$$

Figure 6:
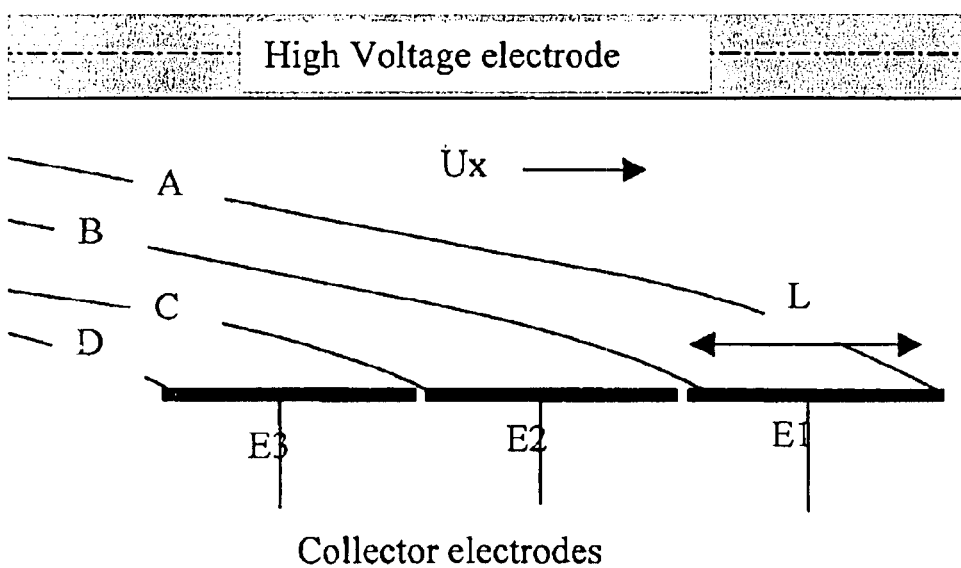
FIG. 6 is a further schematic diagram, illustrating how different particles are collected by different collection electrodes of the DMS of FIG. 1.
Figure 7:
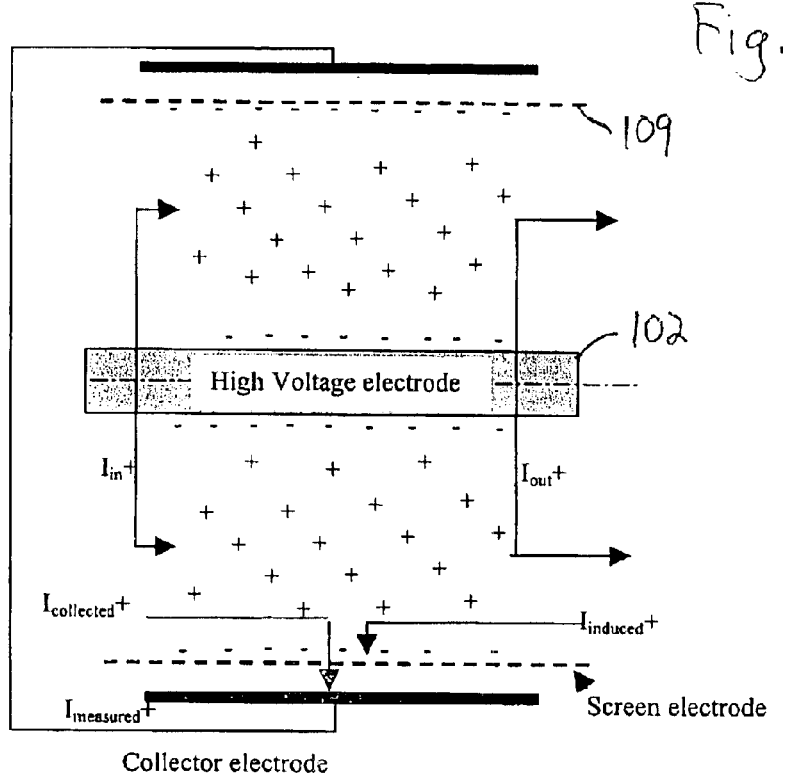
FIG. 7 is a schematic diagram of part of the DMS shown in FIG. 3.

In FIG. 6, there are shown the trajectories of largest particles at end of classifier Where Ux is the flow velocity (⁻1 m/s) and L is the length of the Collector electrode (⁻30 mm)

The column 4 is arranged such that Collector electrode E1 collects the particles with the lowest electrical mobility in the sample (these will be the largest particles—around 1000 nm diameter). These particles follow a trajectory which is within the envelope between A and B in FIG. 6.

$I_{induced1}$ for Collector electrode E1 is caused only by changes in the charge occurring in the flow field immediately adjacent to the ring (between trajectories A and B). All this charge is subsequently collected on the ring, which means that the induced component is negligible ($I_{induced} \approx 0$) and:

$$I_{increased1} \cong I_{collected1} \quad\quad 9$$

The current measured on the previous collector electrode (E2) $I_{measured2}$, similarly has a component $I_{collected2}$ due to particles with mobilities such that their trajectories fall between B and C in FIG. 6. However, the particles which pass Collector electrode E2 without hitting it are the same as those which later hit Collector electrode E1. Changes in the charge on these particles give rise to an induced current on Collector electrode E2, $I_{induced2}$. This current is induced before the particles causing it are detected on the downstream collector electrode by a time equal to the transit time for gas between E2 and E1. The delay time between a particle passing ring m and being collected on ring n is approximately:

$$\delta t_{m,n} = \sum_{n=1}^{m-1} L_n / Ux$$

Where $L_n$ is the length of the collector electrode n and Ux is the axial gas velocity.

The radial location of a charged particle which represents those falling between trajectories A and 8 (ie those that eventually hit the final collector electrode E1) as they pass the penultimate collector electrode (E2) can be estimated from the forces applied to it as it passes through along the classifier. The lost important forces are aerodynamic and the electrostatic forces due to the applied electric field and charge image attraction to surfaces. For the classifier, the applied electric field is large and therefore dominates the induced charge effects in the bulk of the column. The radial entry location is approximately known, as the aerosol all enters near to the High Voltage electrode, and one other point on the path is known to be the location of the final electrode. The electric field can be calculated from Gauss's law. Along with Stokes' theorem (strictly modified by a Cunningham slip correction factor for these small particles) which states that the drift velocity of a particle is proportional to the force on it, this allows the path which the particle follows through the channel to be predicted.

The radial location of particles eventually hitting Collector electrode E1 can be determined along the column by solving:

$$\frac{dr}{dx} = \frac{z_p V_x}{u_x r \ln\left(\frac{r_2}{r_1}\right)} \quad\quad 10$$

where r is the radial location of the particle within the classifier, r2 is the radius of the surface of the High Voltage electrode r1 is the radius of the Collector electrode Vx is the Voltage between the High Voltage electrode and the Collector electrode at position x along the classifier Ux is the axial flow velocity at position x along the classifier For the annular geometry of the classifier, die proportion of charge induced on a given Collector electrode n for a particle at radius r (which is the influence coefficient, K) can be approximated as:

$$Km,n = \left[1 + \frac{\ln\left(\frac{r_{m,n}}{r_2}\right)}{\ln\left(\frac{r_2}{r_1}\right)}\right] \quad\quad 11$$

Where $r_{m,n}$ is the radial location at Collector electrode m of particles which subsequently hit Collector electrode n Note that when the particle is close to the High voltage electrode, K is ~0 and most of the charge is induced on the High Voltage electrode. When the particle is close to the Collector electrode, K is ~1 and most of the charge is induced on the collector electrode. Therefore the component of current measured on Collector electrode E2 ($I_{measured2}$) due to the rate of change of charge passing Collector electrode E2 ($I_{induced2}$) can be calculated from this and the measured rate of change of current on Collector electrode E1 ($I_{measured1}$) using equation 8. The charge adjacent to E2, but not collected on it is (since all of this charge eventually hits E1):

$$\Sigma^+{}_2 = I_{measured\ 1} \times \delta t_{1,2} \quad\quad 12$$

Therefore $$I_{induced_2} = -\delta t_{2,1} K_{2,1} d(I_{measured_1})/dt \quad\quad 13$$

This principle is then extended upstream to the sample entry into the classifier as shown as the correction system in the block diagram in FIG. 2.

The collector electrodes E1 to E4 in this diagram are the four most downstream of the twenty two collector electrodes in the classifier. Collector electrode E1 is furthest downstream, around 600 mm from the most upstream collector electrode. As very few charged particles leave the channel without being measured, the current on collector electrode E1, $I_{measured1}$ indicates the number of particles per unit time ('particle flux') in the aerosol that passed the previous collector electrode E uncollected.

To correct for the transient errors due to the change in particle concentration in the vicinity of Collector electrode E2, the rate of change of the current on Collector electrode E1 (shown by the d/dt box) is multiplied by the appropriate influence coefficient, $K_2$ (from equation 11) and subtracted from the current measured on Collector electrode E2 ($I_{measured2}$). This correction is applied to the value of the current measured on the penultimate electrode E2 a short period earlier and stored, as indicated by the delay blocks in FIG. 2; this delay period being equal to the time taken for the aerosol and sheath flow to travel from the average position of the penultimate electrode to that of the final electrode (which is around 30 ms). Practically, the differentiation operation d/dt may be approximated, for example by a finite difference.

The trajectory down the classifier of charged particles incident on any given Collector electrode can be obtained by solving equation 10. Therefore, the appropriate value of influence coefficient, $K_{m,n}$ for Collector electrode m due to particles eventually hitting a downstream Collector electrode n can be determined from equation 11.

$I_{induction}$ (which is the component of induced current for Collector electrode m due to particles eventually hitting downstream collector electrodes) is a function of time and may be calculated as follows:

$$I_{induced_m}(t) = -\delta t_m \sum_{n=1}^{m-1} K_{m,n} \frac{d(I_{measured_m}(t+\delta t_{m,n}))}{dt} \quad 13$$

This compensation technique could be implemented as an analogue electric circuit, however the most practical implementation is a digitally sampled system as follows. Data may be sampled and stored digitally at intervals equal to δt (if δt is constant). In this case, the delay time effects are achieved by incrementally displacing the stored arrays. Alternatively, if data is sampled at rates either faster or slower than δt, or δt is not constant, then the arrays should be displaced to give close approximations to &t and where this cannot be achieved, an interpolation between datapoints may be required.

Summary

For this embodiment 1 each measured current on a particular Collector electrode is adjusted by subtracting the induced current for that electrode which is determined as the sum of the induced currents due to particles landing on each of the downstream Collector electrodes.

Second Embodiment

The second embodiment of this invention is a modification to a standard electrostatic particle measuring consisting of an additional electrode which screens the sensing electrode or electrodes from the effect of changing charged particle concentrations in the aerosol nearby. This is shown in FIGS. 3 and 7, in which components substantially the same as those of the first embodiment are denoted by the corresponding reference numeral of FIGS. 1 and 5, raised by 100. The symbols used in FIG. 7 have the same meaning as the corresponding symbols used in the description of the first embodiment.

The existing collection electrodes 108 in the instrument are largely covered by an additional, cylindrical shielding electrode 109 which is constructed so that the majority of particles can still pass through it This might be achieved by making the shielding electrode of conductive mesh, gauze, perforated sheet, an array of wires, or similar. The electrical potential of the shielding electrode is controlled (possibly to electrical ground), probably by connecting it to a voltage supply 111. The shielding electrode should be mounted close to the collection electrodes because it eliminates the effect on the collection electrode current of changes in the charged particle density in the aerosol beyond the shielding electrode but not in the volume between the shielding electrode and the collection electrodes. For practical reasons, one shielding electrode may screen one or more collection electrodes or several shielding electrodes may be used The shielding electrode should be designed to impede the flow of charged particles through it as little as possible, so for instance, the open fraction of the gauze should be maximised.

This example uses a single shielding electrode 109 to cover all the ring shaped collection electrodes 108 set unto the outer wall of the channel defined by housing 101. The shielding electrode 109 takes the form of a gauze tube which is supported regularly on electrically insulating rings. The shielding electrode is connected to a voltage supply; the voltage on the shielding electrode should ideally be such that there is still a significant electrostatic field to attract particles from the vicinity of the shielding electrode to the collection electrodes, which must overcome the charge image force that will attract particles to the shielding electrode.

The shielding electrode in this example also reduces the sensitivity of the instrument to changes in the dielectric constant of the gas being measured and to noise in the high voltage supply. The collection electrodes in the DMS carry a constant charge due to the capacitance between them and the centre electrode 102. In the case of the conventional DMS in FIG. 1, changes either in the electrostatic permittivity (due to, for example, water vapour concentration changes) of the aerosol or the voltage on the centre electrode will lead to a change in this charge which will be observed as an erroneous current. The shielding electrode will prevent changes in the permittivity of gas except in the gap between the shielding electrode and collection electrodes from affecting the charge on the collection electrodes, and in the DMS the sample flow remains near the centre of the channel, away from this region. With the shielding electrode fitted, the potential difference which determines the charge on the collection electrodes is now that between the shielding electrode and the collection electrodes, and as this potential difference is smaller, it may be easier to minimise the electrical noise on this voltage.

Collector electrodes 108 comprise rings with an internal diameter of 54 mm and the screen electrode 109 is a mesh tube of thickness about 0.2 mm with diameter 50 mm. Therefore, the screen electrode 109 is spaced from the collector electrodes 108 by about 2 mm.

The screen electrode 109 is maintained at a fixed voltage between that of the high voltage electrode 102 and collector electrodes 108 such that there is an electric field which attracts charged particles through the screen electrode 109 towards the collector electrodes 108. We have operated the screen electrode with a voltage of around +100V.

The charge which is induced by the sample flow is now induced mainly on the high voltage electrode 102 and screen electrode 109 and not on the collector electrodes 108. The primary current flow to the collector electrode 108 from charged particles in the sample passing through the screen 109 and hitting electrodes 108.

The screen electrode 109 mesh size is optimised for reducing the currents induced on the collector electrode, while allowing charged particles to pass through the mesh to the collector electrode. It has been found that a satisfactory size for holes in the mesh is of the same order as the separation between the screen electrode and collector electrode. A mesh made up of triangular holes, with sides of 2 mm, separated by a web of metal of 0.2 mm has been found to give good performance. The screen electrode can be made from thin stainless steel sheet and with an open area of around 80%.

The voltage stability of the screen electrode is very important since changes cause an induced signal on the collector electrode. The support of the screen electrode is important since vibration of the screen electrode relative to the high voltage electrode and collector electrode gives rise to large induced currents on the collector electrode.

Summary

With this embodiment by interposing a screen electrode between the majority of the sample aerosol and the collector electrode, the current measured on the collector electrode is due solely to charged aerosol hitting the collector electrode.

Third Embodiment

Figure 4:
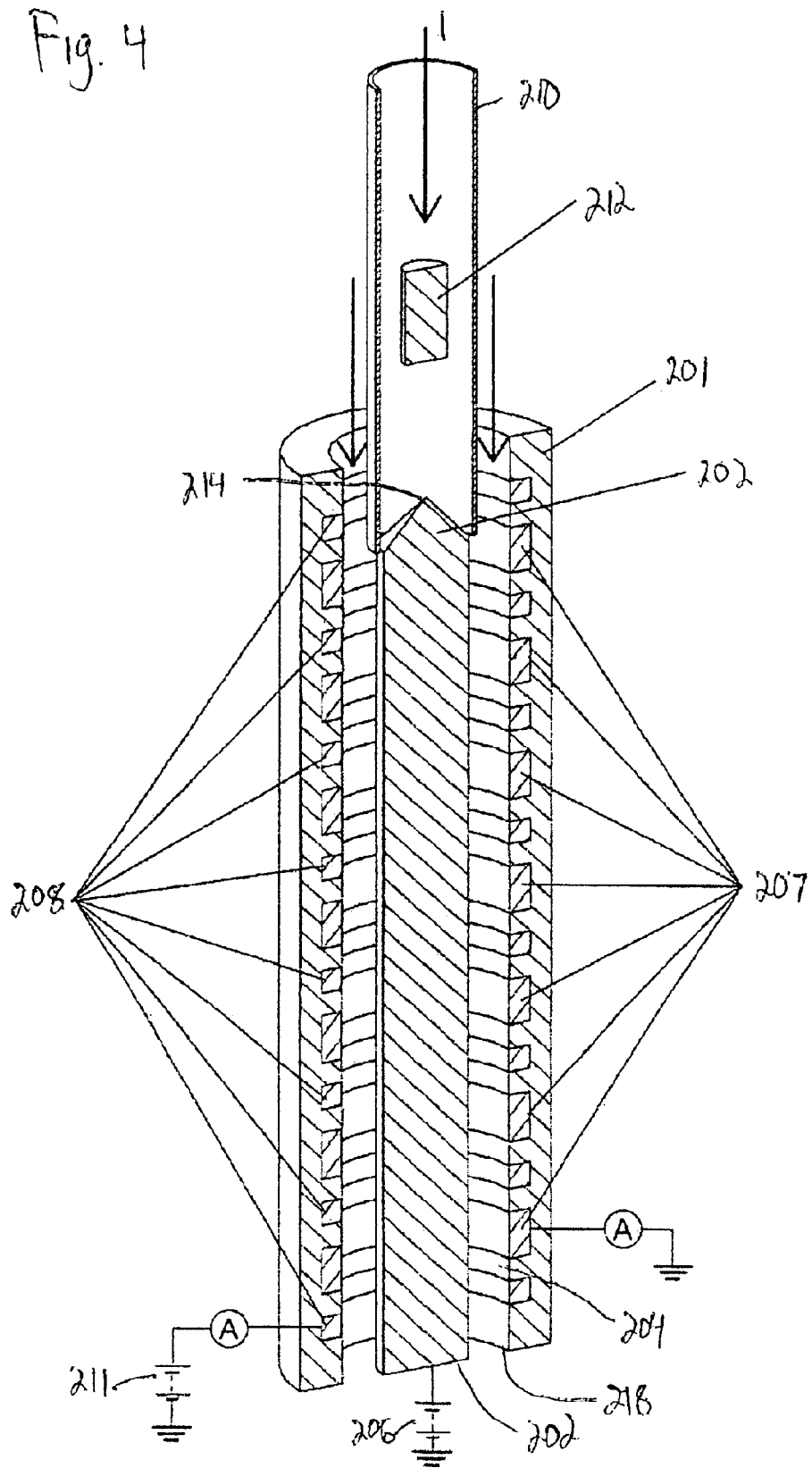
FIG. 4 is a cutaway diagram of a DMS of the third embodiment of apparatus in accordance with the invention.
Figure 8:
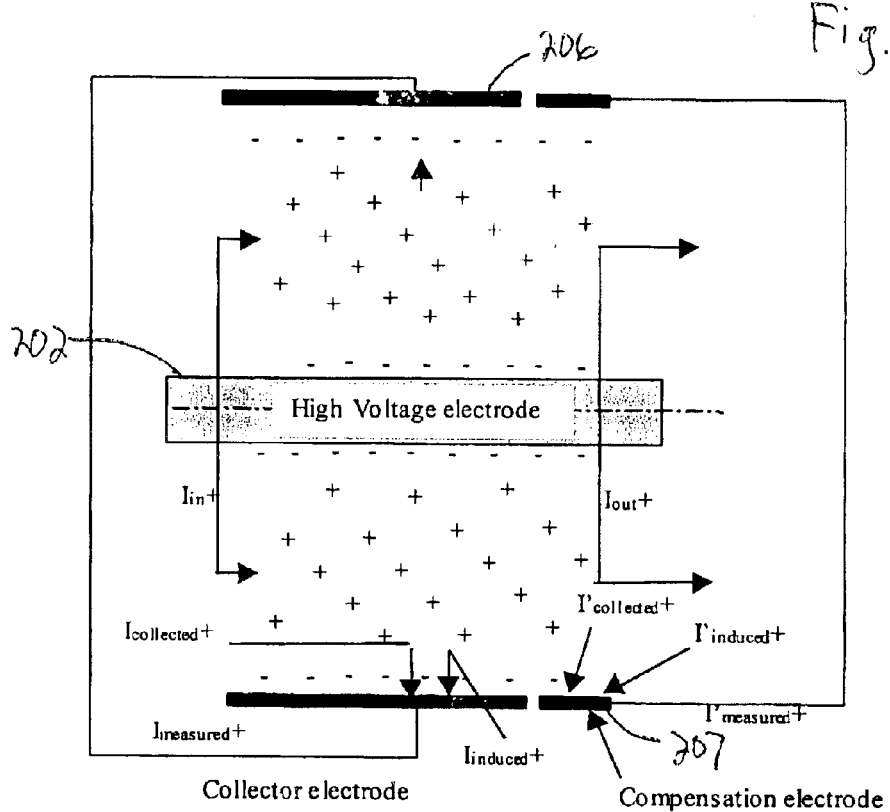
FIG. 8 is a schematic diagram of part of the DMS shown in FIG. 4.

A third embodiment of detector is shown in FIGS. 4 and 8, in which components corresponding to those of the first embodiment are denoted by the reference numerals of FIGS. 1 and 5 raised by 200, the third embodiment includes an addition of compensating electrodes 207 mounted near the collector electrodes 208, in alternating sequence therewith. The electrodes 207 are held at a different potential from the electrodes 208 such that the compensating electrodes do not collect significant numbers of charged particles. The compensating electrodes 207 may be the same size as or a different size to the collection electrodes 208 and should be mounted as close to them as possible. The current flowing to these electrodes is then due only to the rate of change of charged particle density in the aerosol near the electrodes. With appropriate gain to take account of the different sizes of the electrodes, the current measured on the compensating electrodes is subtracted from the current measured on the collection electrodes and thus the effect of changing charged particle concentrations is eliminated.

As can be seen from FIG. 4, the compensating electrodes 207 are mounted between successive collection electrodes 208 in the channel 204. The compensating electrodes 207 are controlled to a voltage such that there is little electric field attracting the charged particles towards them. In FIG. 4, only one such electrical connection is shown for clarity. For the DMS, the compensating electrode voltage should preferably be approximately equal to the voltage of the centre electrode 202. In this example, the correction used for each collection electrode 208, is preferably equal to the average of the currents measured flowing to the electrodes on either side, multiplied by approximately the ratio of the collection electrode length to the compensating electrode length.

In FIG. 8 the flow of charge from particles incident on the Compensation electrode leads to $I'_{collected}+$; the flow of induced charge to the Compensation electrode leads to $I'_{induced}+$; the total charge flow to the Compensation electrode is $I'_{measured}+$ In this implementation, one or more compensation electrodes are introduced adjacent to the collector electrodes. These are maintained at a voltage such that the field at the surface of the electrode acts to repel charged particles in the sample. This requires that the voltage be higher than that for the high voltage electrode. In practice smaller voltages may be used where the collected particles are a very small proportion of those which would have been collected on a ground potential electrode (e.g. 1%) i.e.

$$I'_{collected}+\approx 0$$

Since no charged particles are incident on the compensation electrodes, the signal measured is solely due to the induced charge particles moving in front of the electrodes. For compensation electrodes adjacent to collector electrodes, this means that the induced charge for the collector electrode may he estimated. Where the compensation is shorter than the collector electrode, the compensation should be made per unit length of the compensation electrode.

Where a collector electrode is between two compensation electrodes, the average of the two compensations could be used.

What is claimed is:

1. Apparatus for indicating the quantity of charged particles in an aerosol, the apparatus comprising a sense electrode, the current flow to which is, in use, measured to provide said indication and a shielding electrode mounted near to said sense electrode such that the flow of charged particles from the aerosol towards said sense electrode must pass through said shielding electrode which is constructed to allow the passage of a proportion of said charged particles, said shielding electrode being controlled to an electrical potential relative to said sense electrode, so as to inhibit the effect on the sense electrode of the rate of change in charge density, thereby to eliminate or compensate for the part of the current flowing to said sense electrode which is caused by the rate of change of charge density in said aerosol near said sense electrode.

2. Apparatus according to claim 1, in which the sense electrode is one of a plurality of such electrodes.

3. Apparatus according to claim 2, in which said sense electrodes are mounted along a channel through which said aerosol flows.

4. Apparatus according to claim 2, in which more than one of said shielding electrodes is mounted near said sense electrodes.

5. Apparatus according to claim 3, in which the shielding electrode is tubular and is interposed between the sense electrodes and the channel so that the sense electrodes are situated outside the shielding electrode.

6. Apparatus according to claim 2, in which said sense electrodes are in the form of rings around a channel containing said aerosol and said shielding electrode is in the form of a gauze or similar tube mounted inside said sense electrodes.

7. Apparatus according to claim 1, in which the shielding electrode comprises a conductive grid.

8. Apparatus according to claim 1, in which the shielding electrode comprises a conductive mesh.

9. Apparatus according to claim 1, in which the shielding electrode comprises a perforated conductive sheet.

10. Apparatus according to claim 1, in which the shielding electrode comprises a conductive gauze.

11. Apparatus according to claim 1, in which the shielding electrode comprises an array of wires.

12. Apparatus for analysing a mixture comprising a fluid and a plurality of electrically charged particles wherein, the apparatus comprising a collection element of collecting said particles and providing an output related to the number of particles incident thereon, and a compensation electrode, spaced from the collection element, and responsive to charged particles which pass in the vicinity of, but are not collected by, the collection element, thereby to enable the output from the collection element to be used to determine the charge collected by the collection element, wherein the compensation electrode is mounted immediately downstream of the collection element and the apparatus includes voltage application circuitry for holding the compensation electrode at a potential, relative to the collection element, which is such that it does not collect a significant number of charged particles, the output from said compensation electrode being representative of the induced current on said collection element.

13. Apparatus according to claim 12, in which each collection element comprises a respective collection electrode.

14. Apparatus according to claim 12, in which the collection element is one of a plurality of such collection elements and the compensation electrode is also one of plurality of such compensation electrodes, the compensation electrodes and collection elements being arranged in an alternating sequence along a conduit for conveying the sample.

15. Apparatus according to claim 12, in which the apparatus includes an input for supplying to the apparatus the mixture to be analysed said mixture being in the form of an aerosol of charged particles.

16. Apparatus according to claim 12, in which the apparatus includes a cylindrical conduit for the aerosol, and each collection electrode is annular and positioned co-axially with the conduit.

17. In a method of measuring current flow to a sense electrode to indicate the quantity of charged particles in an aerosol, the improvement comprising the step of eliminating or compensating for the part of the current flowing to said sense electrode which is caused by the rate of change of charge density in said aerosol near said sense electrode, using a screening electrode which is mounted near to said sense electrode such that the flow of charged particles from the aerosol towards said sense electrode must pass through said screening electrode which is constructed to allow the passage of a proportion of said charged particles, said screening electrode being controlled to an electrical potential relative to said sense electrode, so as to inhibit the effect on the sense electrode of the rate of change in charge density.

18. A method according to claim 17, in which the sense electrode is one of a plurality of such electrodes.

19. A method according to claim 18, in which said sense electrodes are mounted along channel through which said aerosol flows.

20. A method according to claim 19, where the flow down said channel includes both said aerosol and an additional flow of gas of no or known particle content.

21. A method according to claim 17, where more than one of said screening electrodes is mounted near said sense electrodes.

22. A method according to claim 17, in which said sense electrodes are in the form of rings around a channel containing said aerosol and said screening electrode is in the form of a gauze or similar tube mounted inside said sense electrodes.

* * * * *